(12) United States Patent
Centeno et al.

(10) Patent No.: US 10,350,372 B2
(45) Date of Patent: Jul. 16, 2019

(54) PERCUTANEOUS DELIVERY DEVICE AND METHOD FOR TENDON-LIGAMENT-MUSCLE REPAIR

(71) Applicant: Regenerative Sciences, LLC, Broomfield, CO (US)

(72) Inventors: Christopher Centeno, Broomfield, CO (US); Patrick Reischling, Broomfield, CO (US); Timothy Snyder, Broomfield, CO (US)

(73) Assignee: Regenexx, LLC, Broomfield, CO (US)

( * ) Notice: Subject to any disclaimer, the term of this patent is extended or adjusted under 35 U.S.C. 154(b) by 155 days.

(21) Appl. No.: 15/107,859

(22) PCT Filed: Jan. 20, 2015

(86) PCT No.: PCT/US2015/012005
§ 371 (c)(1),
(2) Date: Jun. 23, 2016

(87) PCT Pub. No.: WO2015/112486
PCT Pub. Date: Jul. 30, 2015

(65) Prior Publication Data
US 2016/0317760 A1    Nov. 3, 2016

Related U.S. Application Data

(60) Provisional application No. 61/930,155, filed on Jan. 22, 2014.

(51) Int. Cl.
*A61M 5/32*     (2006.01)
*A61M 5/46*     (2006.01)
(Continued)

(52) U.S. Cl.
CPC ........... *A61M 5/46* (2013.01); *A61B 17/3421* (2013.01); *A61B 17/3478* (2013.01);
(Continued)

(58) Field of Classification Search
CPC .......... A61M 5/46; A61M 5/158; A61M 5/32; A61M 5/3286; A61M 25/0082;
(Continued)

(56) References Cited

U.S. PATENT DOCUMENTS 5,762,636 A   6/1998  Rupp
5,860,953 A   1/1999  Snoke
(Continued)

OTHER PUBLICATIONS

STIC search1 Jan. 19, 2018.*
(Continued)

*Primary Examiner* — Laura A Bouchelle
*Assistant Examiner* — Dung T Ulsh
(74) *Attorney, Agent, or Firm* — Adsero IP

(57) ABSTRACT

Embodiments include systems, methods and devices for the percutaneous delivery of therapeutic agents to tendons, ligaments and muscle. Certain embodiments include a device comprising a needle-catheter based delivery system with adjustable characteristics to allow a clinician to control the angle and depth of needle and/or catheter deployment to a desired location. System embodiments may include a controller unit where a clinician can adjust the axial position depth and location of needles and/or catheters.

21 Claims, 6 Drawing Sheets

(51) Int. Cl.
   *A61B 17/00* (2006.01)
   *A61B 17/06* (2006.01)
   *A61B 17/34* (2006.01)
   *A61B 90/00* (2016.01)
   *A61M 25/00* (2006.01)

(52) U.S. Cl.
   CPC .......... *A61M 5/329* (2013.01); *A61M 5/3286* (2013.01); *A61M 5/3287* (2013.01); *A61B 2017/0042* (2013.01); *A61B 2017/00331* (2013.01); *A61B 2017/00455* (2013.01); *A61B 2017/00862* (2013.01); *A61B 2017/00991* (2013.01); *A61B 2017/06076* (2013.01); *A61B 2017/3443* (2013.01); *A61B 2090/067* (2016.02); *A61M 5/3297* (2013.01); *A61M 25/0084* (2013.01); *A61M 2005/3201* (2013.01); *A61M 2205/0266* (2013.01); *A61M 2210/086* (2013.01)

(58) Field of Classification Search
   CPC ...... A61M 25/0084; A61M 2025/0085; A61M 2025/0089; A61M 2025/0091; A61B 2017/3454; A61B 2017/3456; A61B 2017/3458; A61B 2017/346; A61F 2002/30688
   See application file for complete search history.

(56) References Cited

U.S. PATENT DOCUMENTS

| | | |
|---|---|---|
| 2004/0138562 A1 | 7/2004 | Makower et al. |
| 2004/0147877 A1 | 7/2004 | Heuser |
| 2005/0125002 A1* | 6/2005 | Baran ............... A61M 25/0041 606/108 |
| 2005/0277875 A1* | 12/2005 | Selkee ............. A61M 25/0136 604/95.04 |
| 2006/0167416 A1 | 7/2006 | Mathis et al. |
| 2006/0217655 A1 | 9/2006 | Vitullo |
| 2007/0191853 A1* | 8/2007 | Stone ................ A61B 17/1675 606/79 |
| 2010/0280449 A1* | 11/2010 | Alvarez .......... A61B 17/00234 604/95.04 |
| 2011/0054287 A1* | 3/2011 | Schultz .............. A61B 5/0422 600/374 |
| 2011/0276001 A1* | 11/2011 | Schultz ............. A61B 17/3415 604/164.01 |
| 2012/0136385 A1* | 5/2012 | Cully ...................... A61F 2/07 606/194 |
| 2012/0283830 A1* | 11/2012 | Myers ............... A61B 17/0401 623/13.12 |
| 2012/0296345 A1* | 11/2012 | Wack ................ A61B 17/0483 606/139 |
| 2014/0114330 A1* | 4/2014 | Karasic ............ A61B 17/0401 606/144 |
| 2014/0121701 A1* | 5/2014 | Dreyfuss ........... A61B 17/0401 606/232 |
| 2014/0222072 A1* | 8/2014 | Gerber .............. A61B 17/0401 606/232 |
| 2015/0099936 A1* | 4/2015 | Burdulis .......... A61M 25/0194 600/204 |
| 2016/0279388 A1* | 9/2016 | Barrish ............. A61M 25/0155 |
| 2017/0087334 A1* | 3/2017 | Tegg ................. A61M 25/0136 |
| 2017/0120019 A1* | 5/2017 | Goldfard .......... A61M 25/09041 |
| 2017/0224955 A1* | 8/2017 | Douglas ............ A61M 25/0136 |
| 2017/0251905 A1* | 9/2017 | Durant ................ A61B 1/0052 |
| 2017/0274158 A1* | 9/2017 | Saeed Malik ....... A61M 5/3287 |
| 2017/0368304 A1* | 12/2017 | Cole ................. A61M 25/0041 |

OTHER PUBLICATIONS

STIC search2 Jan. 19, 2018.*
International Search Report and Written Opinion dated Apr. 30, 2015 for International Patent Application No. PCT/US2015/012005.
European Extended Search Report, dated Aug. 25, 2017, 6 pages.

* cited by examiner

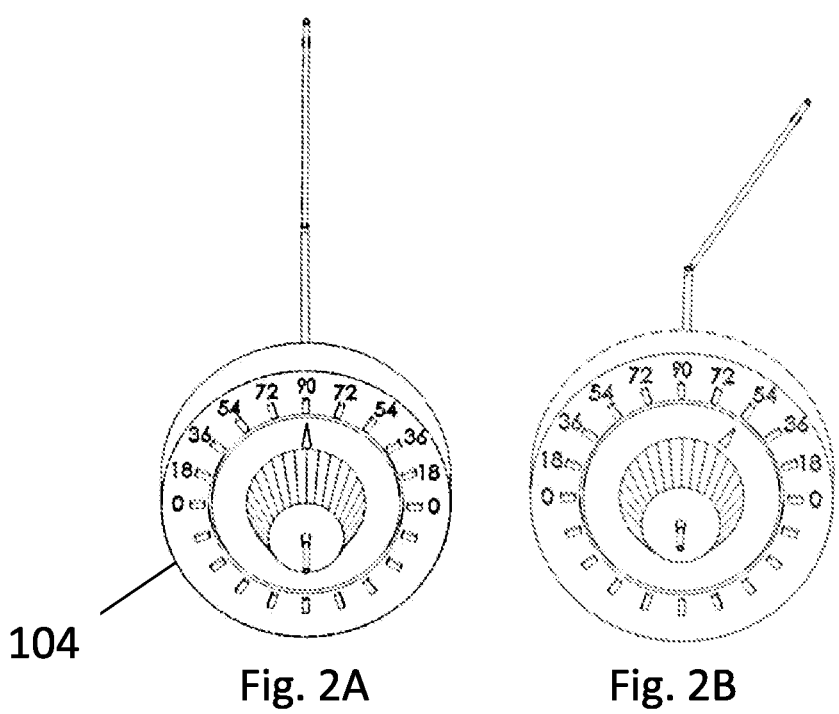

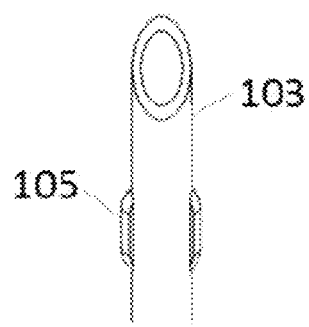
Fig. 3A
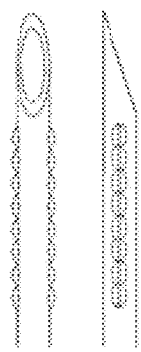 
Fig. 3B
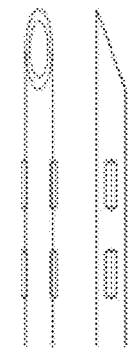
Fig. 3C
Fig. 3D
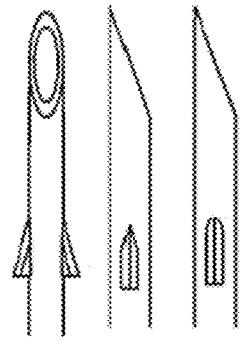
Fig. 3E
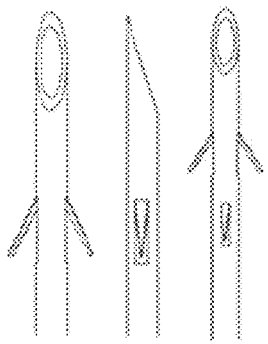
Fig. 3F
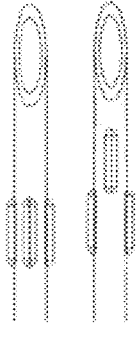
Fig. 3G
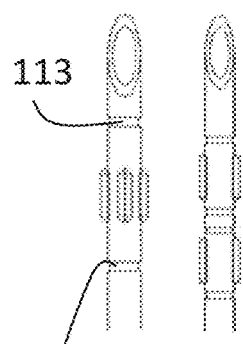
Fig. 3H
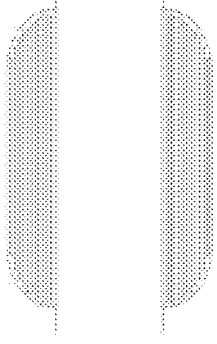
Fig. 3I

PERCUTANEOUS DELIVERY DEVICE AND METHOD FOR TENDON-LIGAMENT-MUSCLE REPAIR

RELATED APPLICATIONS

This application is a 35 U.S.C. § 371 national phase application of PCT/US15/12005 (WO 2015/112486) filed on Jul. 30, 2015, entitled "PERCUTANEOUS DELIVERY DEVICE AND METHOD FOR TENDON-LIGAMENT-MUSCLE REPAIR", which application claims the benefit of U.S. Provisional Application Ser. No. 61/930,155, filed Jan. 22, 2014, which is incorporated herein by reference in its entirety.

TECHNICAL FIELD

The embodiments enclosed herein relate to a device, system and methods for the delivery of therapeutic agents to ligaments, tendons or muscle using a steerable and guided needle-catheter percutaneous device.

BACKGROUND

The use of therapeutic agents for the treatment of ligament, tendon and muscle tissue injury has become increasingly popular as the efficacy for these treatments has become more promising. In addition, the use of percutaneous devices to treat these injuries is highly beneficial for the patient resulting in reduced recovery times, decreased infection rates, improved mobility, and less physical therapy times when compared to traditional reconstruction surgery. As therapeutic agents for treating tendon, ligament and muscle damage progresses, the devices to deliver those agents percutaneously must likewise progress to provide clinicians options to optimally treat their patients.

Tendons, ligaments and muscle provide the mechanical mechanisms and support for the body. Tendons and ligaments are mainly composed of aligned collagenous fibers packaged into bundles. Muscle composition may similarly be bundled into fascicles consisting of aligned myocytes that provide the mechanical energy for movement. Damage to these tissues by means of injury or disease creates serious complications both in the short and long term. In certain tendons, ligaments and muscle the body is limited in repairing the damage based on several factors. For one, the damage may be so extensive that it is beyond repair such as a full thicknesses retracted tear. In other circumstances certain areas of the musculoskeletal system lack vascularity limiting the appropriate immune response for natural healing. To overcome this deficiency, biological agents such as autologous platelet rich plasma, platelet lysate, nucleated cells isolated from the bone marrow or fat, progenitor cells, and mesenchymal or other stem cells percutaneously transplanted to the damaged site have shown in-vitro and in animal studies to aid in the repair process. The localization of therapeutic agents to the damaged site is important to successfully target the tear or lesion. Based on current methods this can be accomplished with great skill under ultrasound or fluoroscopic imaging, however certain anatomical locations are difficult to reach with known techniques.

One such challenge in delivery localization occurs when treating the anterior cruciate ligament (ACL). There is no currently available and published technique for accessing this ligament percutaneously. One option for delivering therapeutic agents to the ACL bundles involves using a needle placed at the interchondylar eminence as verified under fluoroscopic imaging. The ACL emanates from the tibia at this location and this bony landmark provides the clinician with a reference point to treat the tissue. However often times the damaged part of the tissue resides at the proximal region of the ACL where localized delivery would be difficult since there is no fluoroscopic reference point, the delivery needle is normally rigid, and a bent needle or catheter may become misguided to the target.

The following embodiments disclosed herein are directed at overcoming one or more of the problems discussed above.

SUMMARY OF THE EMBODIMENTS

The embodiments disclosed herein describe various systems, methods and devices to achieve the percutaneous delivery of therapeutic agents to tendons, ligaments and muscle that are anatomically difficult to reach using current clinical techniques and devices. In certain embodiments a system is described consisting of modifications to a needle and/or catheter at the distal end capable of using the naturally aligned fibers of the tissue as a guidance mechanism to the target site. Multiple modifications to the tip are disclosed as examples that may achieve this goal. Further embodiments describe a device comprising a needle-catheter based delivery system with adjustable characteristics to allow a clinician to control the angle and depth of needle and/or catheter deployment to a desired location. This system would be designed to give a clinician control of angular deployment in at least two planes providing a means to reach obscure locations. Such a system would consist of a controller unit where a clinician can adjust the needles and/or catheters that would additionally provide feedback as to how much axial and/or depth deployment has occurred. A further embodiment describes a frequency or impulse based mechanism located at the proximal end of the device that could detect different tissue types at the distal end providing a clinician further feedback for adjustments. Throughout, materials and methods will be described to further illustrate the device and its assembly with the overall goal of providing a tool capable of percutaneously reaching damaged tissue in areas that are currently a challenge to target percutaneously.

BRIEF DESCRIPTION OF THE DRAWINGS

FIG. 1B depicts the device in a steeper angle from the longitudinal axis of the outermost hollow tube while FIG. 1C is at a shallower angle with a full range from 0 to 90 degrees.

FIG. 2A and FIG. 2B are schematic diagrams of a controller unit attached to the proximal end of the tubular system. The controller unit is comprised of a dial and settings that allows the user to adjust the angle of deployment of the innermost needle in the coronal plane.

FIGS. 3A-3I disclose an embodiment of the device where the distal end of the innermost hollow tube consists of various projections that would allow the tube to be guided by the aligned fibers of tendons, ligaments or muscles. FIG. 3H further depicts the distal end comprising a propeller like mechanism allowing the projections to rotate about the longitudinal axis as it moves through the tissue.

FIG. 6B depicts the controller unit comprising an internal compartment housing the components that provide the mechanisms for needle/catheter adjustability and feedback display. FIG. 5C provides an overall assembly of the device with the controller unit and needle/catheter system.

DETAILED DESCRIPTION

Figure 1A:
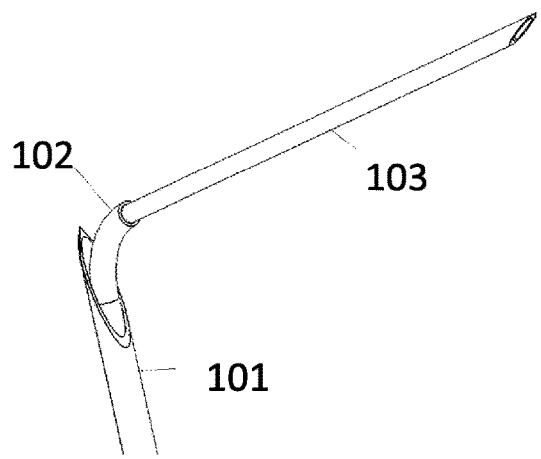
FIG. 1A is an isometric view of one of the embodiments depicting a general configuration of the device at its distal end consisting of three hollow tubes.

Unless otherwise indicated, all numbers expressing quantities of ingredients, dimensions reaction conditions and so forth used in the specification and claims are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

Unless otherwise indicated in this application and claims, the terms needle, cannula, tubular members, telescoping tubes all refer to tubes containing at least a proximal end, distal end and further comprising a lumen. Additionally the tissues in consideration refer to all tissues containing an aligned fibrous structure and may not be limited to tendons, ligaments and muscle.

Minimally invasive procedures are becoming increasingly popular as percutaneous devices and methods are able to treat injuries and diseases that would otherwise require open surgical methods. For example, artificial heart valve replacement can now be accomplished using a balloon tipped catheter inserted into the femoral artery and guided to the target valve without the need of open heart surgery. Research and advances within the past ten years using biological agents to treat orthopedic applications are revealing positive outcomes. Thus, percutaneous methods will reduce the need for current invasive orthopedic surgical procedures i.e. total knee replacement, ACL reconstruction surgery etc.

Known prior art fails to describe a percutaneous system capable of treating inaccessible tendon, ligament or muscle by means of exploiting their anatomical characteristics. In particular, these types of tissue are composed of aligned fiber bundles. The disclosed devices, systems and methods are optimized with an innermost tube comprised of a modified distal tip that follows these fiber bundles from beginning to end. In addition, the orientation of certain tendons, ligaments and muscle requires a system that can align the tubes with that direction. For example the ACL is oriented from the medial to lateral and anterior to posterior direction from tibia to femur. Therefore, the system contains components that can control the angles of tubular deployment to align with the orientation of the tendon, ligament or muscle specific to the patient. Finally, certain embodiments of the disclosed devices comprise components that allow the user to input and/or control the angles of tubular deployment. These angles might be based on analysis of pre-operative imaging and/or procedural imaging of boney landmarks. The embodiments disclosed herein describe such a device and methods in detail with reference to the figures to aid in understanding.

In one embodiment, the system includes at least three hollow concentric tubes as seen in an isometric view in FIG. 1A. The outermost tube 101 consists of a proximal and distal end, where said distal end contains a bevel and acts as an introducer needle into the tissue. The outermost tube 101 comprises a material that is strong enough to pierce tissue. In one embodiment, the outermost tube 101 is made out of stainless steel. The lumen of the outermost tube 101 contains a second hollow tube 102 that coaxially fits within the outermost tube 101. Second hollow tube 102 further comprises a pre-formed curvature at the distal end that may be made of a shape memory material such as Nitinol where the curvature ranges from at least 0 to 90 degrees from the longitudinal axis of the tube. The second hollow tube of 102 contains a third innermost hollow tube 103. The innermost hollow tube 103 is made of a flexible material to follow the bend of second hollow tube 102, strong enough to traverse the tissue, and biologically compatible. Materials may include, but are not limited to, shape memory alloys such as Nitinol or typical catheter polymers such as silicone rubber, nylon, polyurethane, polyethylene terephthalate latex and thermoplastic elastomers.

Figure 1B:
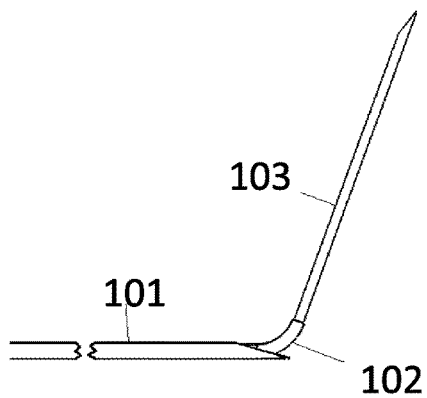
FIG. 1B and FIG. 1C depict the device in two different configurations illustrating the ability of deploying an innermost hollow tube at different angles.
Figure 1C:
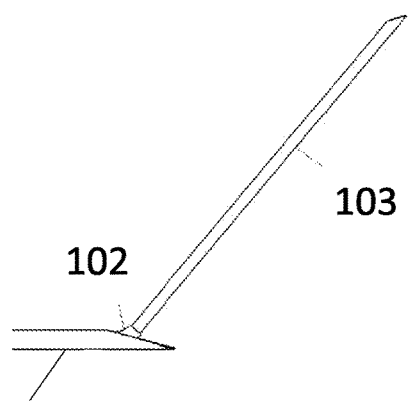

The embodiments described allow the user to control the angle of deployment of the innermost tube 103 as a function of exposure of second hollow tube 102 from outermost tube 101. For example, FIG. 1B depicts second hollow tube 102 being exposed from the outer tube 101 creating a relatively steep angle for the deployment of innermost tube 103 from the longitudinal axis. FIG. 1C depicts the second hollow tube 102 less exposed from outermost tube 101, relative to FIG. 1B, thus creating a shallower angle relative to the outermost tube 101. When the radius of curvature of tube 102 fully extends from tube 101, the maximum angle is achieved and is at least 90 degrees from the axis of the outermost tube 101. If tube 102 is fully retracted within tube 101 the angle of deployment is parallel to the outermost tube 101. This provides the user to control a range of angular motion from 0 to 90 degrees in the plane of the outermost tube 101.

Figure 6A:
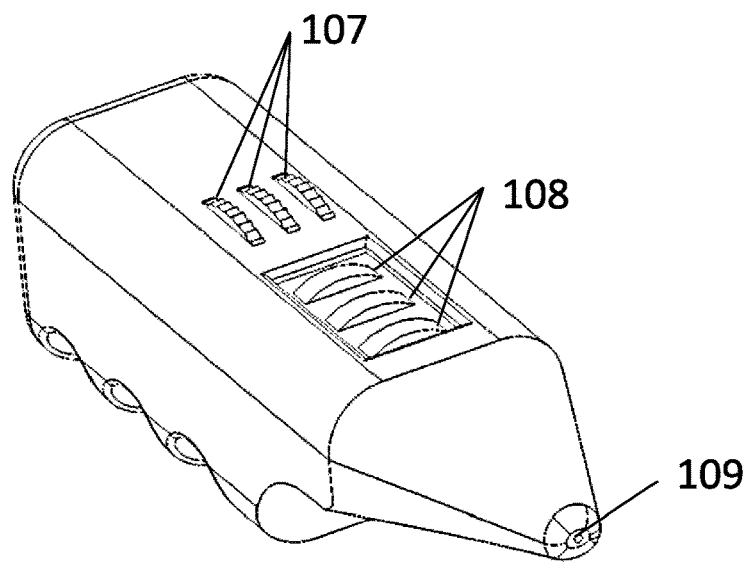
FIGS. 6A-6C is a schematic diagram of another embodiment of the disclosed device with an advanced handheld controller unit allowing a clinician to control the angles and deployment of the needle/catheter system in multiple planes. The controller unit comprising switches, levers, gears, or dials for the clinician to adjust the needles/catheters and further comprising displays to show the amount of adjustment that occurred.
Figure 6B:
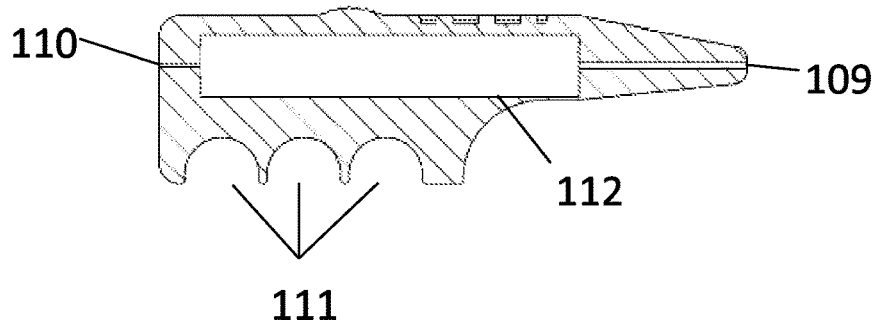

In one embodiment, the device is used to treat the ACL. In the sagittal plane the ACL was measured to have a mean angle of 58.7+/−3.8 degrees when measured with reference to the tibial plateau. In the coronal plane the ACL was measured to have a mean angle of 65.9+/−4.4 degrees with reference to the tibial plateau. The measurements were made from MRI imaging analysis of healthy patients with their knee in extension. It is expected that an injured, partial or full tear of the ACL would affect these average angles and thus patient variability must be accounted for. Therefore the embodiments described provide a means to deploy an innermost tube 103 with the angle of the ACL as seen in FIG. 6A and FIG. 6B. In one embodiment, the clinician obtains data from pre-operative imaging that provide the angles of ACL in the coronal and sagittal planes. The measured angles may be obtained from a CT or MRI image that is post-processed using computer aided software and/or analyzed by an expert. In other embodiments, the clinician may obtain the angles from bony landmarks under fluoroscopy such as the interchondylar eminence of the tibia and resident's ridge of the femur.

By knowing the general angles of the ACL in both planes the device allows a user to deploy an innermost tube parallel with the ACL. FIG. 2 depicts a controller apparatus 104 according to one embodiment. The controller apparatus 104 is attached to a proximal region of the device. The controller apparatus 104 contains a dial that can be used to set the angle of the second hollow tube 102 to the angle of the ACL in the coronal plane. A person having ordinary skill in the art will appreciate that other means can be used to set the angle of the second hollow tube 102, and that the above described dial is a non-limiting example for illustrative purposes.

The deployment of the innermost tube can then be aligned with the ACL in both the coronal and sagittal plane as described by the following example. In one embodiment, the outermost tube 101, containing second hollow tube 102 and innermost tube 103 coaxially within, is introduced to the intra-articular space using current practices. Under fluoroscopy the user can locate the interchondylar eminence and place the outermost tube within this region representing the base of the ACL. The device would be originally aligned with a deployment angle of 90 degrees, parallel with the longitudinal axis of the patient as seen in FIG. 2A. If the angular measurements of the ACL was determined to 54 degrees in the coronal plane the apparatus 104 could be dialed to a notch rotating the tubular system and making the deployment angle parallel with the ACL as seen in FIG. 2B. The apparatus could then lock in this angle while the user adjusts the angle in the sagittal plane. The user retracts the outermost tube 101 exposing second hollow tube 102 to the desired angle. In another embodiment the user can extend second hollow tube 102 out of outermost tube 101 to the desired angle. It may be more beneficial to be able to retract outermost tube 101 from second hollow tube 102 as this would reduce the amount of punctured tissue. This sets the correct angle for deployment in the sagittal plane as seen in FIG. 7B. Once the angles have been set, tube 103 extends into the ACL to reach the proximal region. The placement can be verified by fluoroscopy possibly in conjunction with contrast medium. The proximal region of the innermost tube 103 comprises an attachment apparatus to assemble a syringe containing therapeutic agents that can be injected to the targeted location at the distal end of 103.

In another embodiment of the device, the innermost tube 103 consists of projections 105 extruding at the distal end. Ligaments and tendons are comprised of collagen fibrils with diameters ranging from 40 to 150 nm. These fibrils are bundled into collagen fibers with diameters ranging from 1 to 20 micrometers. The collagen fibers are then bundled into fascicles that range in diameter from 360 to 1500 micrometers. The bundles are aligned in the axial direction of the ligament or tendon to uphold the forces generated by the moving joint or muscle. The projections 105 extruding from the distal end may be of various sizes and geometries, including, but not limited to, the depictions in FIGS. 3A to 3I. The projections are designs that catch between the bundles and guide the innermost tube in the direction of the aligned bundles. These may be any of the bundles described above. For example the projections can range in size from 360 to 1500 micrometers to fit and catch between the larger bundles. Furthermore, the projections may contain ridges, grooves or perturbations on them ranging in size from 1 to 20 micrometers to catch the smaller collagen fibers. Therefore the tissue provides the structure in which the innermost tube 103 can follow.

FIG. 3A is a diagram of the general concept of a projection at the distal end of the innermost tube. In alternative embodiments the function of the projection may be fulfilled with a groove, track or other structure configured to catch fibers or bundles. FIG. 3B shows aligned projections linked one after the other on both sides of the innermost tube. FIG. 3C depicts two projections aligned and spaced by a certain distance on opposing sides of the innermost tube. FIG. 3D shows projections in a random orientation spaced out from each other a desired amount. FIG. 3E depicts wing shaped projections that may be sharply or smoothly rounded at the top then fanned out like a wing with a straight bottom. FIG. 3F portrays similar wing geometry but extracts from the main tube and may consist of multiple extrusions at different locations and numbers on the innermost tube. FIG. 3G represents projections that may be rounded at the proximal and distal end of the projection and may be in different quantities and geometries. FIG. 3H illustrates another embodiment where the innermost tube consists of a rotation mechanism 113 about the longitudinal axis at the distal end. The rotation mechanism 113 allows the projections to then freely rotate about the longitudinal axis as it is fed through the tissue to account for irregularities in the alignment of the bundles. This can be viewed as a propeller like mechanism to more cohesively interact with the tissue. FIG. 3H provides two examples of these sections at the distal end capable of freely rotating and comprising the projection examples 105. FIG. 3I depicts the projections comprised with fine grooves ranging in size and spaced 1 to 20 micrometers apart. This would allow additional interaction with the finer aligned bundles of the tissue. FIG. 3 provides examples that would allow the tube to be guided through the tissue and is not limiting to other designs capable of accomplishing that task. In addition the embodiments include any combinations to the projections proposed. For example, the ideal design may be a combination of the placement of the projections in FIG. 3D, consist of the projection geometry like that of FIG. 3G and further consist of the freely rotating mechanism of FIG. 3H.

Figure 4:
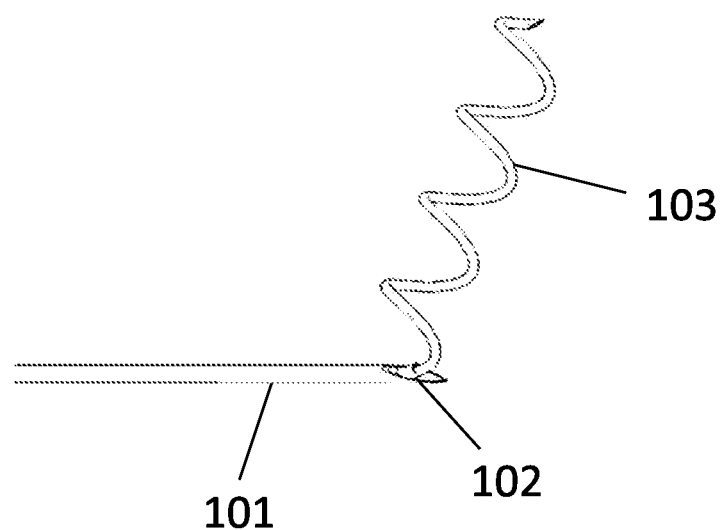
FIG. 4 is a schematic diagram of the innermost hollow tube capable of traversing through the ligament, tendon or muscle in a spiral manner by means of a cork-screw shape. This hollow tube may further comprise the guiding projections at the distal end described in FIG. 3.

In another embodiment of the device, the innermost needle 103 may have a pre-formed shape made of a shape memory material like Nitinol that would traverse the tissue by other means than parallel to the longitudinal axis of the tendon. FIG. 4 is a schematic diagram of an embodiment of the device where the innermost tube is pre-formed in a spiral formation where the tube would traverse the tissue in a cork-screw manner. This may provide the user with the ability not only to reach the proximal region of the ACL, but possibly reach the outer edges of the tissue as well. A tube in this configuration may also reduce the risk of the tube becoming misguided from the tissue since it would continually wind back towards the tissue as it deploys from its outer tube. Embodiments may also consist of the projections at the distal end as described in FIG. 3.

Figure 5:
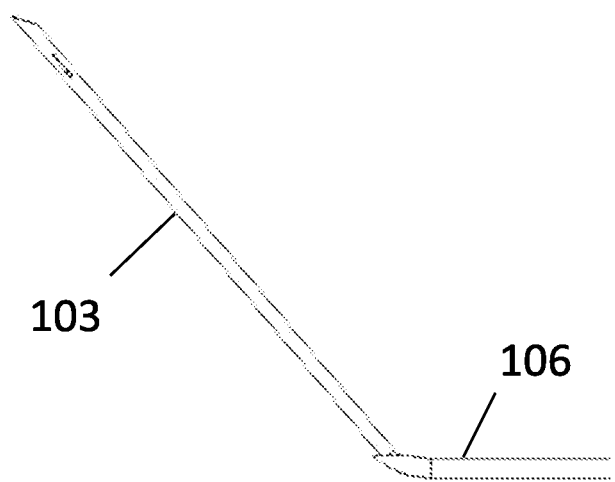
FIG. 5 is a schematic of another embodiment of the device where the system is comprised of only two hollow tubes. One outer tube comprising an angled distal end and the inner hollow tube comprised of a Nitinol shape memory material in a pre-formed shape and/or comprising the guiding modifications at the distal end as described in FIG. 2.

In another embodiment, the tubular system may consist of only two hollow tubes. FIG. 5 depicts a two hollow tube system comprising an outer hollow tube 106 where the exit at the distal end is angled in a pre-formed direction. This is similar to a tuohy needle where the user can use the obtained angle measurements and choose from a variety of outer tubes with manufactured angles at the distal end that match the ACL in the sagittal plane. The outermost tube 106 could then be rotated with the aid of apparatus 104 in FIG. 2 to control the angle in the coronal plane. Therefore with a selection of outer tubes and apparatus 104 this two hollow tube system can still set the angle of deployment in both the coronal and sagittal planes. Embodiments of this system also include projections from innermost tube 103 as outlined in FIG. 3 and may also include a pre-formed shape like that of FIG. 4.

A further embodiment of the device consists of an advanced manual controller unit attached to the tubular system allowing the user full control of the system. FIG. 6A is an isometric view of the manual controller unit according to one embodiment. The controller unit consists of knobs, dials, gears or other controls 107 allowing the user to adjust the angle and length of deployment of the innermost tube. The user may have control of the angle in at least one plane, which may be the only controllable aspect. In some embodiments, the controller can adjust the amount of deployment and/or the angle of deployment of at least one of the hollow tubes. In other embodiments, the controller can adjust the amount and angle of deployment of all of the tubes. The user will also have a feedback display 108 that shows the amount of the adjustment to give the user better control. One display may show the degree of angular adjustment, while another may show how much the hollow tube has been displaced i.e. amount of deployment. The controller unit may consist of at least one knob, dial or gear 107 and at least one display 108. FIG. 6A depicts a controller with three adjustable knobs and three displays that would allow the user to control the amount of the deployment of the innermost tube as well as the angle of deployment in the sagittal and coronal planes.

FIG. 6B is a schematic diagram of an exemplary embodiment of a manual controller unit. The tubular system protrudes from the controller unit at 109 while the innermost tube will exit the unit at 110. This exit will allow the user to attach a syringe to the innermost tube to dispense therapeutic agents within to reach the target site at the distal end of the tube. The controller unit may also consist of a grip 111 for easier handling. Further the unit will contain a compartment 112 containing the mechanical components that provides the mechanisms to adjust the tubular system. This might include gears, springs, actuators, electromechanical components, and tubular holders to accomplish the desired mechanisms for control. FIG. 6B provides an example design only and is not limiting. The unit could be of a much different size, shape and configuration with the basic idea of controlling the tubular members.

Figure 6C:
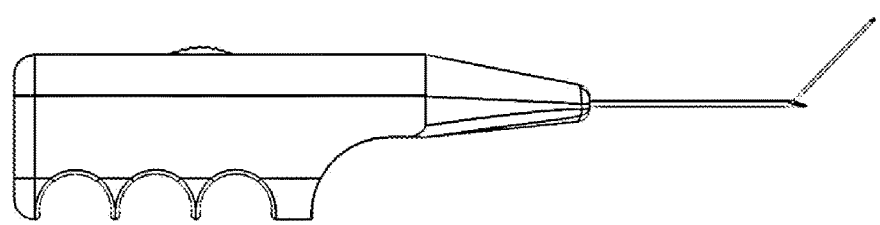

FIG. 6C is a diagram of the exemplary controller unit with the tubular system attached. In one embodiment the tubular system is pre-attached and packaged with the tubular system where all components are sterile and disposable. In another embodiment the controller unit may be non-disposable and the user attaches the tubular system to the unit. In one embodiment, this is accomplished by simply feeding the tubes through the opening 109 where the tubes are then firmly held by tubular holders like a rubber washer. In another embodiment, a mechanism is used where the controller unit can open along a seam and the tubular system placed inside.

Figure 7A:
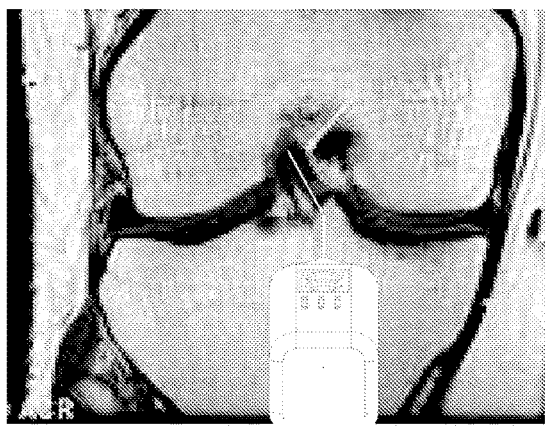
FIG. 7A is a coronal MRI of the knee joint with the disclosed device depicting the capability of the needle/catheter system to reach the proximal end of the ACL with angular control in the coronal plane.
Figure 7B:
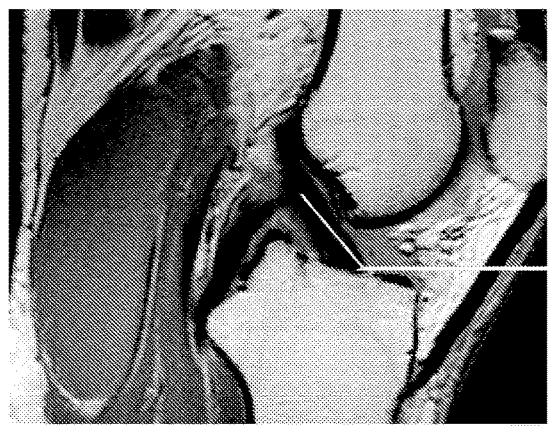
FIG. 7B is a sagittal MRI of the knee joint with the disclosed device depicting the capability of the needle/catheter system to reach the proximal end of the ACL with angular control in the sagittal plane.

FIG. 7 illustrates the system being used to treat the ACL. The described device will allow the user to reach the proximal region of the ACL by having control of the angle of deployment of the innermost needle and the innermost needle comprising projections at the distal end for self-guidance within the aligned bundles of the tissue.

The description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A device for percutaneous use comprising:
   a tubular system having at least two hollow tubes, the tubular system comprising:
      an outer tube having a first proximal end, a first hollow shaft, and a first distal end; and
      an innermost tube, the innermost tube having a second proximal end, a second hollow shaft, and a second distal end, the innermost tube being housed coaxially within the first hollow shaft of the outer tube, the innermost tube configured to advance within the first hollow shaft of the outer tube, and wherein the second distal end of the innermost tube exits the first distal end of the outer tube, wherein the innermost tube comprises a plurality of projections at the second distal end, the plurality of projections aligned to engage ligament, tendon, or muscle fiber bundles and configured to guide the second distal end of the innermost tube along the axial direction of the ligament, tendon, or muscle fiber bundles, without flexing toward the innermost tube, as the innermost tube is advanced in the axial direction into the ligament, tendon, or muscle fiber bundles; and
   a controller apparatus operatively coupled to the tubular system, the controller apparatus configured to adjust an angle of deployment of the tubular system in a coronal plane, and further to adjust an angle of deployment of the innermost tube in a sagittal plane independently from the outer tube, the controller apparatus further configured to adjust a length of deployment of at least one of the tubes of the tubular system.

2. The device of claim 1, wherein the second distal end of the innermost tube comprises a pre-formed curvature having a shallowest angle when fully retracted, and a steepest angle when fully extended from the first distal end.

3. The device of claim 1, wherein the first distal end of the outer tube is angled in a preformed direction that guides the innermost tube as the second distal end exits the first distal end at the preformed angle of the first distal end.

4. The device of claim 1 wherein:
   the tubular system further comprises an inner tube having a third proximal end, a third hollow shaft, and a third distal end, the inner tube housing the innermost tube in the third hollow shaft.

5. The device of claim 4, wherein the third distal end of the inner tube comprises a pre-formed curvature having a shallowest angle when fully retracted, and a steepest angle when fully extended from the first distal end.

6. The device of claim 1, wherein the innermost tube further comprises a rotation mechanism near the second distal end that allows the plurality of projections to freely rotate perpendicular to a longitudinal axis of the innermost tube.

7. The device of claim 1, wherein the plurality of projections at the second distal end of the innermost tube comprise a size and geometry that interacts with the fiber bundles to allow the innermost tube to self-navigate in the direction of the bundles, wherein the size and geometries are selected from a group comprising sharp, rounded, pointed, smooth, wing-shaped, tines, square, rectangular, half-circular, and triangular.

8. The device of claim 1, wherein the plurality of projections comprise grooves, ridges, or perturbations that further interact with smaller fiber bundles of tissue to aid in self-guidance of the innermost tube.

9. The device of claim 1 wherein the controller apparatus comprises one or more components to control the deployment length and the deployment angles of the innermost tube.

10. The device of claim 1 wherein the controller apparatus comprises one or more knobs or dials providing for adjustment of the deployment length and the deployment angles of the tubular system.

11. The device of claim 1, wherein the controller apparatus comprises a visual display providing deployment length and deployment angle adjustment feedback.

12. The device of claim 1, wherein the innermost tube is formed in a substantially helical spiral shape.

13. The device of claim 1 wherein the outer tube comprises a needle tip having at least one of the following tip types, Quincke, Touhy, beveled, Whitacre, and pencil point.

14. The device of claim 1 wherein at least one of the first, second, or third distal tips are echogenic.

15. The device of claim 1 wherein the at least one of the at least two tubes of the tubular system are visible using fluoroscopy.

16. The device of claim 1 wherein the innermost tube is comprised of at least one of a memory metal, steel, a carbon steel, a surgical steel, or a polymer plastic.

17. The device of claim 16 wherein the innermost tube is comprised of memory metal, and the memory metal comprises at least one of copper-zinc-aluminum-nickel, copper-aluminum-nickel, or nickel-titanium.

18. The device of claim 16 wherein the innermost tube is comprised of polymer plastic, and the polymer plastic comprises at least one of silicone rubber, nylon, polyurethane, polyethylene terephthalate latex or thermoplastic elastomers.

19. A method for percutaneous treatment of the proximal region of an anterior cruciate ligament (ACL) comprising:
providing a device for percutaneous use comprising:
a tubular system having at least two hollow tubes, the tubular system comprising:
an outer tube having a first proximal end, a first hollow shaft, and a first distal end; and
an innermost tube, the innermost tube having a second proximal end, a second hollow shaft, and a second distal end, the innermost tube being housed coaxially within the first hollow shaft of the outer tube, the innermost tube configured to advance within the first hollow shaft of the outer tube, and wherein the second distal end of the innermost tube exits the first distal end of the outer tube, wherein the innermost tube comprises a plurality of projections at the second distal end, the plurality of projections aligned to engage ligament, tendon, or muscle fiber bundles and configured to guide the second distal end of the innermost tube along the axial direction of the ligament, tendon, or muscle fiber bundles; and
a controller apparatus operatively coupled to the tubular system, the controller apparatus configured to adjust an angle of deployment of the tubular system in a coronal plane, and further to adjust an angle of deployment of the innermost tube in a sagittal plane independently from the outer tube, the controller apparatus further configured to adjust a length of deployment of at least one of the tubes of the tubular system;
determining an angle of the ACL preoperatively;
aligning the outer tube with the determined angle of the ACL in at least one plane;
deploying the outer tube into the ACL substantially aligned with the determined angle of the ACL;
deploying the innermost tube from the outer tube; and
positioning the innermost tube to a proximal region of the ACL, the positioning step comprising;
adjusting an angle of the innermost tube along a second plane perpendicular to the at least one plane;
engaging a ligament, tendon, or muscle fiber bundle with at least one of the plurality of projections from the innermost tube;
guiding the innermost tube along the ligament, tendon, or muscle fiber bundle with at least one of the plurality of projections from the innermost tube; and
deploying therapeutic agents through the innermost tube to the proximal region of the ACL.

20. The method of claim 19 wherein the outer tube is aligned by the controller apparatus to the determined angle of the ACL in the coronal plane of the ACL.

21. The method of claim 20 wherein the innermost tube is aligned by the controller apparatus to a selected angle in the sagittal plane of the ACL.

* * * * *